United States Patent [19]
Mikulicz et al.

[11] 3,959,402
[45] May 25, 1976

[54] SEPARATION OF HF FROM POLYMER, CONSTANT BOILING MIXTURE RELIEF GASES AND VENT GASES IN ALKYLATION PROCESS

[75] Inventors: Michael Z. Mikulicz, Palatine; William G. Boney, Rolling Meadows; Bipin V. Vora, Burralo Grove, all of Ill.

[73] Assignee: Universal Oil Products Company, Des Plaines, Ill.

[22] Filed: Dec. 11, 1974

[21] Appl. No.: 531,514

[52] U.S. Cl. .......................................... 260/683.48
[51] Int. Cl.² .......................................... C07C 3/54
[58] Field of Search ............... 260/683.48; 683.42

[56] References Cited
UNITED STATES PATENTS

| | | | |
|---|---|---|---|
| 2,322,800 | 6/1943 | Frey | 260/683.48 |
| 2,432,030 | 12/1947 | Matuszak | 260/683.48 |
| 2,448,601 | 9/1948 | Kelley | 260/683.48 |
| 2,493,384 | 1/1950 | Bergen | 260/683.48 |
| 2,542,927 | 2/1951 | Kelley | 260/683.48 |
| 3,243,474 | 3/1966 | Cole, Jr. | 260/683.48 |

Primary Examiner—Delbert E. Gantz
Assistant Examiner—G. J. Crasanakis
Attorney, Agent, or Firm—James R. Hoatson, Jr.; Robert W. Erickson; William H. Page, II

[57] ABSTRACT

HF-containing vent gases, relief gases, CBM and polymers discharged from the alkylation zone of an HF alkylation process are contacted with water. Hydrogen fluoride is absorbed within the water, reacted with olefins, converted to organic fluorides and returned to the alkylation zone of the process. HF leaving the alkylation process in vent gases, relief gases, CBM and polymers is thereby recovered.

3 Claims, 1 Drawing Figure

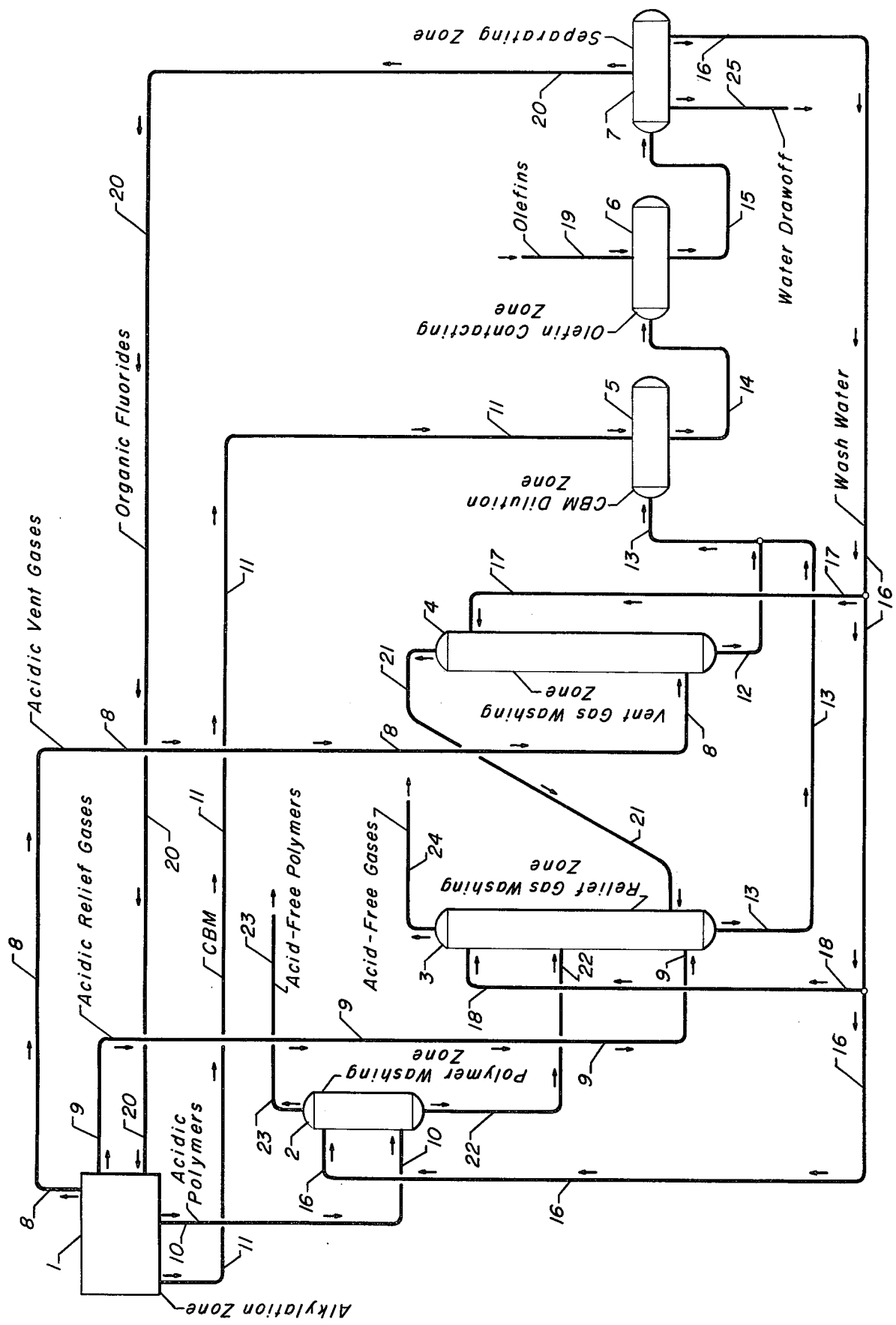

3,959,402

SEPARATION OF HF FROM POLYMER, CONSTANT BOILING MIXTURE RELIEF GASES AND VENT GASES IN ALKYLATION PROCESS

BACKGROUND OF THE INVENTION

1. Field of the Invention

The field of art to which this invention pertains is hydrocarbon processing. It particularly relates to an improved HF alkylation process in which HF loss is reduced.

2. Prior Art

The importance of higher molecular weight isoparaffins, having valuable antiknock properties, is increasing with the present progressive restrictions upon the lead content of gasoline. A convenient source of such higher molecular weight isoparaffins is the catalytic alkylation of lower boiling isoparaffins, such as isobutane, with olefins such as propene and butenes. Catalytic alkylation using hydrofluoric acid has become an important tool for preparing motor fuel blending components.

Hydrofluoric acid is a hazardous chemical with properties peculiar to itself which call for special handling and treatment. With improper treatment it can be lethal. For this reason processes for its use must be equipped with systems which effectively prevent its escape into the atmosphere. Common practice in the art is to chemically treat HF-containing streams which discharge from alkylation processes.

Treating processes in current use counter-currently contact acidic gases with an aqueous solution of a metal hydroxide, such as potassium hydroxide, within an elaborate plate-type contact tower. Where KOH is used as the metal hydroxide, KF is formed.

The resulting aqueous KF solution is further contacted with $Ca(OH)_2$ to precipitate $CaF_2$ which is highly insoluble in water. The fluoride precipitate, in the form of a sludge, is then disposed of as waste.

Operators of these prior art processes must replenish the HF lost by chemical treatment of waste gases. The disposal of a precipitate sludge also poses an inconvenience to the processor.

Acidic liquids discharging from prior art HF alkylation processes are commonly passed to a receptacle, such as a pit, where they are contacted with $Ca(OH)_2$ for neutralization. HF in these liquids is not recovered from the precipitated $CaF_2$ and is, therefore, lost.

HF can be recovered from exiting acidic gases and liquids facilly and economically by the use of our invention. HF loss from the process and the HF replenishment which loss necessitates are thereby greatly reduced. The use of elaborate and inconvenient prior art processes involving the disposal of treatment wastes is also avoided by use of the present invention.

BRIEF SUMMARY OF THE INVENTION

Our invention involves a process for the recovery of hydrogen fluoride prior to disposal of HF-bearing gases and liquids discharging from the alkylation zone of an HF alkylation process. Wash water absorbs HF from the gases and liquids. Absorbed HF is reacted with olefins to form organic fluorides. Organic fluorides are returned to the alkylation zone. The washed gases and liquids are discharged, being substantially free from HF.

OBJECTS AND EMBODIMENTS

It is an object of this invention to remove hydrogen fluoride from gaseous and liquid mixtures containing the same.

Still another object of our invention is to provide an HF-catalyzed hydrocarbon alkylation process with reduced HF loss.

In one embodiment our invention affords an improved, hydrogen fluoride-catalyzed alkylation process of the type in which acidic vent gas, acidic relief gas, CBM and acidic polymer streams are produced in an alkylation zone, wherein THE IMPROVEMENT COMPRISES (i) contacting the acidic vent gas, acidic relief gas, CBM and acidic polymer streams with wash water; (ii) absorbing HF from said acidic vent gas, acidic relief gas, CBM and acidic polymer streams into said wash water to form a wash water-HF mixture; (iii) reacting said wash water-HF mixture with an olefin stream to form organic fluorides; (iv) separating said organic fluorides from said wash water, and passing said organic fluorides to said alkylation zone.

BRIEF DESCRIPTION OF THE DRAWING

The attached drawing illustrates a particular embodiment of the present invention. Only such details are included as are necessary for a clear understanding of our invention, and no intention is thereby made to unduly limit its scope. Certain items necessary to the operation of the process but unnecessary to its understanding, such as certain process streams, valves, pumps, instrumentation and other equipment have been omitted for the sake of clarity.

Referring now to the drawing, acidic vent gases, containing HF, exit alkylation zone 1 in conduit 8 and pass to vent gas washing zone 4, where contact with wash water is effected, and at least a portion of the HF in the acidic vent gases is absorbed by the wash water. Washed vent gases exit the vent gas washing zone in conduit 21, passing to relief gas washing zone 3, where further contact with wash water takes place.

Acidic relief gases exit alkylation zone 1 in conduit 9, passing to relief gas washing zone 3. HF in the acidic relief gases and washed vent gases entering the relief gas washing zone in conduits 9 and 21, respectively, are cleansed of HF through contact with wash water in the relief gas washing zone. Gases free from HF exit the relief gas washing zone in conduit 24.

Acidic polymers exit alkylation zone 1 in conduit 10 and pass to polymer washing zone 2 where contact with wash water removes substantially all of the HF contained within the acidic polymers. Acid-free polymers exit the polymer washing zone in conduit 23.

A constant boiling mixture called CBM, an azeotrope of HF and water, exits alkylation zone 1 in conduit 11, passing to CBM dilution zone 5. A dilute mixture of HF and water enters the CBM dilution zone in conduit 13, intimately intermixing with the CBM. A resultant mixture exits the CBM dilution zone in conduit 14, passing to olefin contacting zone 6.

Olefins in conduit 19 enter the olefin contacting zone and therein react with the HF contained in the HF-water mixture from conduit 14. A resultant two-phase mixture of olefins, organic fluorides and water exits the olefin contacting zone in conduit 15, passing to separating zone 7.

The two-phase mixture entering separating zone 7 in conduit 15 is separated into an aqueous phase and a hydrocarbonaceous phase. The aqueous phase, substantially free from HF, exits the separating zone in conduits 16 and 25. The hydrocarbonaceous phase, comprising olefins and organic fluorides exits the separating zone in conduit 20, passing to alkylation zone 1. Sufficient wash water is withdrawn in conduit 25 to maintain a constant inventory of water in the system.

The aqueous phase exiting separating zone 7 in conduit 16 passes to the various washing zones of the process as wash water. A portion of the wash water exits conduit 16 in conduit 17 and passes to vent gas washing zone 4. Another portion of the wash water in conduit 16 exits in conduit 18 and passes to relief gas washing zone 3. The remaining portion of wash water in conduit 16 passes to polymer washing zone 2. After contact with acidic polymers in polymer washing zone 2, the wash water, now containing absorbed HF, exits the polymer washing zone in conduit 22 and passes to relief gas washing zone 3. Wash water and HF exit the relief gas washing zone in conduit 13 and combine with wash water and HF from the vent gas washing zone which enters conduit 13 in conduit 12. Combined wash water and HF then enter the CBM dilution zone in conduit 13.

DETAILED DESCRIPTION OF THE INVENTION

Hydrofluoric acid is among the most hazardous of all the widely used industrial chemicals because of its effect upon all living body tissues. It is harmful in practically any concentration in either liquid or vapor form. Hydrofluoric acid breaks down, in aqueous solutions, into hydrogen and fluorine which are present as what are known as hydrogen ions and fluorine ions. hydrofluoric acid causes a surface burn to bodily tissues through the action of the hydrogen ions. In addition, the fluorine ions penetrate below the surface and continue to attack and destroy tissue and bone until they are precipitated as magnesium or calcium fluoride by the action of magnesium or calcium compounds present in the body or administered in medical treatments. The fluorine ions effect deep seated, ulcerous sores which commonly resist therapeutic efforts. The effect of the acid upon skin and mucus tissue is to cause extreme pain which often occurs only after the acid has been absorbed below the surface, such that washing is largely ineffective. This effect is commonly known to personnel of hydrogen fluoride processes as "delayed-action burn".

The character of HF makes it essential that it not be released into the atmosphere. For this reason elaborate and costly systems are designed into process plants to collect the gaseous and liquid discharges from the processes which may contain HF and remove the HF from them before conduction to waste disposal or other facilities which communicate with the environment.

Such gases and liquids discharging from HF alkylation processes are comprised, primarily, of acidic relief and vent gases, acidic polymers and CBM. Relief gases result from the opening of relief valves within the plant. When a relief valve associated with an acid-bearing processing zone opens, it exhausts acid gases into the relief system which conducts the gases to treating facilities for removal of acidic components. Vent gases result from the depressuring, cleansing and gas-blanketing of unit operations equipment, often in preparation for mechanical maintenance. The acidic materials remaining within a broken pump, for example, are vented and purged from the pump through special conduits which conduct the acidic materials and the purging medium to the vent system.

Polymers are byproducts of the HF alkylation process and require disposal. polymers form within the alkylation zones of conventional processes and, because these materials are contaminants with respect to the catalyst, they must be removed. It is common in the art to continuously remove polymers from the HF catalyst by distillation. A stream composed of polymers, dissolved HF and an azeotropic mixture of HF and water, called CBM or "constant boiling mixture", is commonly removed from the HF catalyst as the bottoms product of a distillation or stripping tower. The CBM phase and the polymer phase of this stream are often separated, the CBM neutralized with $Ca(OH)_2$ and the polymers and dissolved HF burned in the atmosphere. This burning of acidic polymers releases HF into the environment.

Prior art processes used for treatment of relief and vent gases for removal of HF generally involve contact of the gases with a liquid treating medium and subsequent regeneration of the treating medium. The resultant waste product, usually in the form of a precipitate sludge of a metal fluoride is inconvenient to handle and discard. Common practice in the art is to use special vehicles, equipped with vacuum actuated retrieval systems, to aspirate the sludge into tanks for its translation to a place of disposal. The cost and complexity of operation of these prior art HF removal processes, combined with the irrecoverable loss of HF in the sludge which they produce and the release of HF into the biosphere make them a source of bother and inconvenience to operators of HF alkylation process plants.

Our invention provides an HF alkylation process which is an advance over the prior art by virtue of the inclusion of zones for recovery of HF from exiting gases and liquids.

The process of our invention comprises an alkylation zone, zones for water washing acidic polymers, acidic vent gases and acidic relief gases, a zone for diluting CBM, an olefin contacting zone and a separation zone. The alkylation zone may be any of the designs well known in the art which provides for contact of alkylatable and olefinic hydrocarbon species with HF alkylation catalyst for the production of alkylated hydrocarbon products.

A characteristic of HF alkylation zones is the production of the aforementioned acidic vent gases, acidic relief gases, acidic polymers and CBM, containing HF. In the process of our invention acidic polymers pass to a polymer washing zone where they are contacted with wash water to remove HF. The polymer washing zone may be a bubble-cap plate or sieve plate tower. Counter-current contact of water and polymers is preferred. The conditions of operation are governed by the temperature necessary to maintain the polymer in a liquid state and of a sufficiently low viscosity for effective passage through a plate tower. This depends upon the characteristics of the particular polymer being treated, however, we prefer to operate the polymer washing zone between about 100°F and 200°F. The pressure required is any convenient pressure which will be above the vapor pressure of the two-phase polymer-water mixture within the polymer washing zone. This is necessary to prevent boiling from taking place within the zone. Acid-free polymers are withdrawn from the polymer washing zone for disposal. A mixture of wash water and HF is withdrawn from the polymer washing zone and is sent to a relief gas washing zone for participation in the washing of acidic relief gases.

Acidic vent gases from the alkylation zone pass to a vent gas washing zone which may be a plate or packed type of contact tower. Counter-current contact is effected between the acidic vent gases and wash water in order to absorb HF into the wash water. We prefer to use a temperature between about 40°F and 100°F in this zone in order to maximize absorption of HF in the wash water. The pressure in this zone is normally dependent upon the pressure of downstream systems into which acid-free vent gases are discharged. Washed vent gases are withdrawn from the vent gas washing zone and passed to the relief gas washing zone for further contact with wash water.

Acidic relief gases from the alkylation zone and washed vent gases from the vent gas washing zone enter the relief gas washing zone, which may be a plate or packed type of tower arranged for counter-current flow of wash water and gases. Wash water removes essentially all of the HF from the gases within this zone. Acid-free gases are withdrawn from the relief gas washing zone for disposal. Substantially the same conditions of temperature and pressure should be maintained within the relief gas washing zone as in the vent gas washing zone.

Wash water, after absorbing HF, is withdrawn from the relief gas washing zone and the vent gas washing zone and combined before passing it to a CBM dilution zone.

CBM, an azeotropic mixture of water and HF which commonly contains about 50 wt. % HF, is passed from the alkylation zone to the CBM dilution zone. The wash water-HF mixtures entering the CBM dilution zone from the relief gas washing zone and the vent gas washing zone should be maintained at HF concentrations significantly below 50 wt. %, and preferably below 10 wt. %. The CBM and the wash water-HF mixtures are combined within the CBM dilution zone, resulting in a dilution of the CBM. Dilution of the CBM is necessary to avoid the occurance of undesirable polymerization reactions which might occur in a downstream olefin contacting zone were such a high concentration of HF contacted with olefins. The CBM dilution zone may be a closed vessel with internally disposed flow restrictions such as baffles or perforated plates or any other of the many devices used in the art to thoroughly mix two liquid streams. The resulting mixture of wash water CBM and HF, composed of water and HF, is withdrawn from the CBM dilution zone and passed to an olefin contacting zone.

Olefins are contacted with the water-HF mixture within the olefin contacting zone in order to remove HF from the water and to recover HF in a form in which it may be reused in the alkylation zone. Upon contact between olefins and dissolved HF within the olefin contacting zone, organic fluorides are formed, which organic fluorides are believed to be intermediate products of the alkylation reactions taking place within the alkylation zone. For this reason the organic fluorides may be returned to the alkylation zone for participation therein. The olefin contacting zone should be a closed vessel of the type widely used in the art to thoroughly mix immiscible liquids. Such a vessel may be vertically or horizontally disposed and may be fitted with internal perforated plates, nozzles, baffles or other means for interdispersing the olefin phase with the aqueous phase within the vessel.

Olefins suitable for use in the olefin contacting zone may be the olefins in use in the alkylation zone, provided they are mono-olefins, such as propene or butenes. We prefer to use mono-olefins rather than those with more than one double bond because mono-olefins are much less likely to polymerize in the presence of an HF-water mixture than are, for instance, di-olefins.

The olefin-organic fluoride-water mixture within the olefin contacting zone is passed to a separating zone where the mixture is separated into an aqueous phase and a hydrocarbonaceous phase. The aqueous phase is withdrawn from the separation zone and is passed as wash water to the vent gas washing zone, the relief gas washing zone and the polymer washing zone. The hydrocarbonaceous phase, comprising organic fluorides and olefins, is withdrawn from the separation zone and passed to the alkylation zone. To prevent the accumulation of water entering the system in the CBM, a water drainoff stream is removed from the separation zone.

An example of the operation of the embodiment shown in the appended drawing, in which butene is used as the required olefin, is as shown in Table I and Table II, below. Table I shows a material balance, and Table II represents the operating conditions of the several zones of our invention. Stream and vessel designation numbers correspond to those of the drawing.

TABLE I

| Conduit No. | HF, lbs/day | H₂O, lbs/day | Hydrocarbons lbs/day | Organic Fluoride lbs/day |
|---|---|---|---|---|
| 8 | 26.4 | | 178.1 | |
| 9 | 1,319.3 | | 11,081.8 | |
| 10 | 3.0 | | 147.0 | |
| 11 | 38.0 | 38.0 | | |
| 23 | | | 147.0 | |
| 24 | | | 11,259.9 | |
| 19 | | | 38,827.6 | |
| 20 | | | 34,945.1 | 5,269.2 |
| 16 | (at 7) | 27,734.0 | | |
| 25 | | 38.0 | | |
| 17 | | 528.0 | | |
| 18 | | 26,386.0 | | |

TABLE II

| Zone No. | 2 | 3 | 4 | 5 | 6 | 7 |
|---|---|---|---|---|---|---|
| Polymer Washing Zone: °F. | 150 | | | | | |

TABLE II-continued

| Zone No. | 2 | 3 | 4 | 5 | 6 | 7 |
|---|---|---|---|---|---|---|
| psig. | 50 | | | | | |
| Relief Gas Washing Zone: °F. | | 80 | | | | |
| psig. | | 5 | | | | |
| Vent Gas Washing Zone: °F. | | | 80 | | | |
| psig. | | | 7 | | | |
| CBM Dilution Zone: °F. | | | | 100 | | |
| psig. | | | | 75 | | |
| Olefin (Butene) Contacting Zone: °F. | | | | | 110 | |
| psig. | | | | | 75 | |
| Separating Zone: °F. | | | | | | 110 |
| psig. | | | | | | 75 |

We claim as our invention:

1. In a hydrogen-fluoride-catalyzed alkylation process wherein polymer is formed during said process and wherein a constant boiling mixture of HF and water, relief gases containing HF and vent gases containing HF are collected during said process, the method of recovering hydrogen fluoride from said polymer, said constant boiling mixture and said gases comprising:
   a. separately washing said gases with water streams to absorb HF into the water;
   b. stripping HF from hydrogen fluoride catalyst and removing said polymer as bottoms from said stripping step;
   c. washing said polymer with water to absorb HF into the water;
   d. commingling the water streams of step (a) and the water from step (c) with said constant boiling mixture;
   e. adding a mono-olefin to the resultant mixture of step (d) to react said mono-olefin with the hydrogen fluoride therein to form organic fluoride;
   f. separating the reaction mixture of step (e) into an aqueous phase and a hydrocarbon phase containing organic fluoride, and
   g. supplying said hydrocarbon phase to the alkylation zone of said process to form alkylate product therein.

2. The method of claim 1 further characterized in that said aqueous phase from step (f) is supplied as said water streams in step (a) and said water in step (c).

3. The method of claim 1 further characterized in that the reaction mixture of step (e) is separated into an aqueous phase and a hydrocarbon phase comprising organic fluoride and unreacted olefin and said hydrocarbon phase is supplied to said alkylation process.

* * * * *